(12) United States Patent
Fache

(10) Patent No.: US 7,041,848 B2
(45) Date of Patent: May 9, 2006

(54) METHOD FOR OXIDIZING HYDROCARBONS INTO ACIDS

(75) Inventor: Eric Fache, Caluire et Cuire (FR)

(73) Assignee: Rhodia Polymide Intermediates, Saint Fons (FR)

( * ) Notice: Subject to any disclaimer, the term of this patent is extended or adjusted under 35 U.S.C. 154(b) by 0 days.

(21) Appl. No.: 10/221,108

(22) PCT Filed: Mar. 7, 2001

(86) PCT No.: PCT/FR01/00686

§ 371 (c)(1),
(2), (4) Date: Dec. 2, 2002

(87) PCT Pub. No.: WO01/66502

PCT Pub. Date: Sep. 13, 2001

(65) Prior Publication Data

US 2003/0166967 A1    Sep. 4, 2003

(30) Foreign Application Priority Data

Mar. 8, 2000    (FR) .................................. 00 02996

(51) Int. Cl.
*C07C 51/16*    (2006.01)
*C07C 51/31*    (2006.01)

(52) U.S. Cl. ...................................... 562/543; 562/542

(58) Field of Classification Search ................ 562/542, 562/543, 416, 412, 509
See application file for complete search history.

(56) References Cited

U.S. PATENT DOCUMENTS 2,223,493 A * 12/1940 Loder .......................... 562/543
3,907,881 A    9/1975 Kuhlmann
4,032,569 A    6/1977 Onopchenko et al.
6,147,256 A    11/2000 Costantini et al.

FOREIGN PATENT DOCUMENTS

EP    0 824 962    2/1998
FR    2 732 678    10/1996
GB    628 457    11/1944
WO    WO 00/46172    8/2000

OTHER PUBLICATIONS

Solomons, Oragnic Chemistry, 1980, John Wiley & Sons, Inc., 2nd ed.p. 96-97 and 659-660.*
Aldrich catalog, 1998-1999, p. 296.*

* cited by examiner

*Primary Examiner*—Cecilia J. Tsang
*Assistant Examiner*—Taylor Victor Oh
(74) *Attorney, Agent, or Firm*—Buchanan Ingersoll, P.C.

(57) ABSTRACT

The present invention relates to a process for oxidizing hydrocarbons, in particular branched or unbranched saturated aliphatic hydrocarbons, cycloaliphatic or alkylaromatic hydrocarbons to acidic or polyacidic compounds.

The invention relates more particularly to the oxidation, with an oxidizing agent containing molecular oxygen, of cyclohexane to adipic acid, in the presence of organic acid of lipophilic nature and in the absence of adipic acid. The separation and recycling of the unoxidized cyclohexane, the oxidation intermediates and the catalysts are easier than in the presence of acetic acid.

17 Claims, No Drawings

METHOD FOR OXIDIZING HYDROCARBONS INTO ACIDS

The present invention relates to a process for oxidizing hydrocarbons, in particular branched or unbranched saturated aliphatic hydrocarbons, cycloaliphatic or alkylaromatic hydrocarbons to acids or polyacids.

The invention relates more particularly to the oxidation, with an oxidizing agent containing molecular oxygen, of cyclohexane to adipic acid.

The oxidation of cyclohexane to adipic acid is a process which has been studied for many years. Specifically, adipic acid is an important chemical compound used as a starting material in many manufactures, such as the production of polymers, for instance polyamides, polyesters or polyurethanes.

Several processes for manufacturing adipic acid from hydrocarbons such as benzene, phenol, cyclohexene and cyclohexane have been proposed.

The oxidation of cyclohexane either directly or in two steps are the routes that are most advantageous for producing adipic acid.

Thus, patent U.S. Pat. No. 2,223,493 published in December 1940 discloses the oxidation of cyclic hydrocarbons to the corresponding diacids, in a liquid phase generally comprising acetic acid, at a temperature of at least 60° C., using a gas containing oxygen and in the presence of an oxidation catalyst such as a cobalt compound.

Many other patents and articles disclose this reaction for the direct oxidation of cyclohexane to adipic acid. However, in order to obtain yields that are acceptable for the production of adipic acid, these documents disclose the use of acetic acid as solvent, in the presence either of a homogeneous catalyst or of a heterogeneous catalyst. Mention may be made, by way of illustration, of the article published in the journal "Chemtech", 555–559 (September 1974), in which the author K. Tanaka summarizes and discusses the process for the direct oxidation of cyclohexane. Mention may also be made of patents U.S. Pat. Nos. 3,231,608, 4,032,569, 4,158,739, 4,263,453 and 5,321,157 and patent EP-A-0 870 751 which disclose various homogeneous catalytic systems.

Processes have also been proposed for the direct oxidation of cyclohexane in the presence of a heterogeneous catalyst such as aluminophosphates substituted with cobalt, for instance in European patent No. EP-A-0 519 569.

The choice of solvent, namely acetic acid, is an important characteristic for obtaining an acceptable degree of conversion of cyclohexane and an acceptable production of adipic acid. The use of such a solvent has many drawbacks brought about, for example, by its corrosive nature under the temperature and pressure conditions used. Furthermore, the use of this solvent poses many problems for the steps of separating out and extracting the adipic acid produced and for the recycling of various compounds.

Specifically, in the presence of acetic acid, it is difficult to separate out and extract from the reaction medium the compounds obtained as by-products of the oxidation such as the cyclohexanone and cyclohexanol formed.

In addition, the extraction of adipic acid by crystallization and its purification are made difficult because the cold solubility of this acid is higher at 25° C. in acetic acid and lower at 80° C. in acetic acid than in water.

The separation and recycling of the homogeneous catalyst are also difficult in the presence of acetic acid. Specifically, firstly, recycling the catalyst without extracting it does not make it possible to maintain a sufficient catalytic activity, and secondly, the operations for separating out the catalyst before recycling as disclosed in particular in French patents Nos. 2 722 783 and 2 746 671 are complex and expensive.

Furthermore, this solvent demands the implementation of a difficult and expensive dehydration of the reaction medium.

A number of processes have also been proposed for the one-step oxidation of cyclohexane to adipic acid without using acetic acid. Some of them propose carrying out this reaction in the absence of solvents, while others are performed with solvents such as organic esters, for instance acetates (U.S. Pat. No. 4,098,817), acetone (U.S. Pat. No. 2,589,648) or alcohols, for instance butanol, methanol or cyclohexanol, or acetonitrile (EP-A-0 784 045).

These processes generally lead to very low selectivities towards adipic acid. Moreover, the solvents used are usually of low stability under the conditions for oxidizing the hydrocarbon such as cyclohexane. This low stability results in large consumption of the solvent, which makes such processes unexploitable.

One of the aims of the present invention is to propose a process for the one-step oxidation of hydrocarbons to produce acids or polyacids, in a medium which is liquid under the conditions of the oxidation reaction and which allows a separation of the acid produced and a recycling in particular of the catalyst by simple operations.

To this end, the invention proposes a process for oxidizing substituted or unsubstituted, saturated aliphatic or cycloaliphatic hydrocarbons or alkylaromatic hydrocarbons to acids or polyacids in a liquid medium by an oxidizing agent comprising molecular oxygen, characterized in that one of the constituents of the liquid medium is an acidic organic compound which is insoluble in water, or which is of lipophilic nature.

According to the invention, the lipophilic acidic compound is a compound which must form, under the temperature and pressure conditions of the oxidation reaction, at least one homogeneous liquid phase with the hydrocarbon(s) to be oxidized. Thus, the lipophilic acidic compound may advantageously be at least partially miscible with the hydrocarbon(s) to be oxidized, under the temperature and pressure conditions used to carry out the oxidation reaction.

The expression "at least partially miscible" means that, under the conditions of the oxidation reaction, the solubility of one compound in the other is at least greater than 2% by weight, and in that at least one homogeneous liquid phase comprising at least some of the hydrocarbons to be oxidized and of the lipophilic acid compound is formed.

In one preferred embodiment of the invention, the miscibility between the hydrocarbon and the lipophilic acid compound is such that, under the conditions in which the invention is carried out, these two compounds form a single homogeneous liquid phase.

The expression "lipophilic acid compound which is suitable for the invention" means aromatic, aliphatic, arylaliphatic or alkylaromatic organic compounds comprising at least 6 carbon atoms, which may comprise several acidic functions and which are of low solubility in water, i.e. they have a solubility of less than 10% by weight at room temperature (10° C.–30° C.).

However, it is possible, without departing from the context of the invention, to use organic compounds whose solubility in water is greater than that indicated above if the coefficient of partition of this compound between the organic phase(s) of the reaction medium which consist essentially of the hydrocarbon to be oxidized, the oxidation intermediates and the non-organic phase comprising the water formed during the oxidation reaction makes it possible to obtain a concentration of the lipophilic organic compound in the said aqueous phase of less than 10% by weight.

Lipophilic organic compounds which may be mentioned, for example, are hexanoic acid, heptanoic acid, octanoic acid, 2-ethylhexanoic acid, nonanoic acid, decanoic acid, undecanoic acid, dodecanoic acid, stearic acid (octadecanoic acid) and the permethyl derivatives thereof (total substitution of the hydrogen atoms of the methylene groups with methyl groups), 2-octadecylsuccinic acid, 2,5-di-tert-butylbenzoic acid, 4-tert-butylbenzoic acid, 4-octylbenzoic acid, tert-butyl hydrogen ortho-phthalate, naphthenic or anthracenic acids substituted with alkyl groups, preferably of tert-butyl type, substituted phthalic acid derivatives, and fatty diacids such as fatty acid dimer. Mention may also be made of acids belonging to the above families and bearing various electron-donating substituents (groups containing a hetero atom such as O or N) or electron-withdrawing substituents (halogens, sulphonimides, nitro or sulphonato groups or the like).

According to another characteristic of the invention, the concentration of lipophilic acidic compound in the reaction medium is determined so as to obtain a molar ratio between the number of moles of lipophilic acid and the number of moles of metal forming the catalyst of between 0.5 and 100 000 and preferably between 1 and 1 000.

The concentration of lipophilic acidic compound in the liquid oxidation medium may vary within a wide range. Thus, it may be between 1% and 99% by weight relative to the total weight of the liquid medium and more advantageously it may be between 10% and 80% by weight of the liquid medium.

It is also possible, without departing from the context of the invention, to use the lipophilic acidic component in combination with another compound which may especially have the effect of improving the production efficiency and/or the selectivity of the reaction for the oxidation to adipic acid, and in particular the dissolution of oxygen.

Examples of such compounds which may be mentioned in particular are nitrites, hydroxyimide compounds and halo compounds, more advantageously fluoro compounds. As compounds that are more particularly suitable, mention may be made of nitrites, for instance acetonitrile or benzonitrile, imides belonging to the family disclosed in patent application EP-A-0 824 962, and more particularly N-hydroxysuccinimide (NHS) or N-hydroxyphthalimide (NHPI), halogenated derivatives such as dichloromethane, fluoro compounds such as:

cyclic or acyclic fluoroaliphatic or perfluoroaliphatic hydrocarbons and fluoroaromatic hydrocarbons, such as perfluorotoluene, perfluoromethylcyclohexane, perfluorohexane, perfluoroheptane, perfluorooctane, perfluorononane, perfluorodecalin, perfluoromethyldecalin, $\alpha,\alpha,\alpha$-trifluorotoluene or 1,3-bis-(trifluoromethyl) benzene;

fluoro or perfluoro esters such as alkyl perfluorooctanoates and alkyl perfluorononanoates;

fluoro or perfluoro ketones such as perfluoroacetone, fluoroalcohols or perfluoroalcohols such as perfluorohexanol, perfluorooctanol, perfluorononanol, perfluorodecanol, perfluoro-t-butanol, perfluoroisopropanol or 1,1,1,3,3,3-hexafluoro-2-propanol, fluoronitriles or perfluoronitriles such as perfluoroacetonitrile, fluoro acids or perfluoro acids such as trifluoromethylbenzoic acid, pentafluorobenzoic acid, perfluorohexanoic acid, perfluoroheptanoic acid, perfluorooctanoic acid, perfluorononanoic acid or perfluoroadipic acid, fluoro or perfluoro halides such as perfluoroiodooctane and perfluorobromooctane, fluoroamines or perfluoroamines such as perfluorotripropylamine, perfluorotributylamine or perfluorotripentylamine.

The oxidation is generally carried out in the presence of a catalyst. This catalyst advantageously comprises a metal element chosen from the group comprising Cu, Ag, Au, Mg, Ca, Sr, Ba, Zn, Cd, Hg, Al, Sc, In, Tl, Y, Ga, Ti, Zr, Hf, Ge, Sn, Pb, V, Nb, Ta, Cr, Mo, W, Mn, Tc, Re, Fe, Ru, Os, Co, Rh, Ir, Ni, Pd, Pt, lanthanides such as Ce and combinations thereof.

These catalytic elements are used either in the form of compounds that are advantageously at least partially soluble in the liquid oxidation medium under the conditions in which the oxidation reaction is carried out (homogeneous catalysis), or are supported on, absorbed or bound to an inert support such as silica or alumina, for example (heterogeneous catalysis).

The catalyst is preferably, especially under the conditions in which the oxidation reaction is carried out:
either soluble in the hydrocarbon to be oxidized,
or soluble in the lipophilic acidic compound,
or soluble in the hydrocarbon/lipophilic acidic compound mixture forming a liquid phase which is homogeneous under the conditions in which the reaction is carried out.

According to one preferred embodiment of the invention, the catalyst used is soluble in one of these media at room temperature or at the temperature at which these media are recycled into a further oxidation.

The term "soluble" means that the catalyst is at least partially soluble in the medium under consideration.

In the case of a heterogeneous catalysis, the catalytically active metal elements are supported on or incorporated into a microporous or mesoporous mineral matrix or into a polymer matrix or are in the form of organometallic complexes grafted onto an organic or mineral support. The term "incorporated" means that the metal is an element of the support or that the process is performed with complexes that are sterically trapped in porous structures under the conditions of the oxidation.

In one preferred embodiment of the invention, the homogeneous or heterogeneous catalyst consists of salts or complexes of metals from groups IVb (the Ti group), Vb (the V group), VIb (the Cr group), VIIb (the Mn group), VIII (the group of Fe or Co or Ni) and Ib (the Cu group) and cerium, alone or as a mixture. The preferred elements are, in particular, Co and/or Mn and/or Cr and/or Zr, Hf, Ce and/or Zr, Hf. The concentration of metal in the liquid oxidation medium ranges between 0.00001% and 5% (% by weight) and preferably between 0.001% and 2%.

The invention applies more particularly to the oxidation of cycloaliphatic compounds such as cyclohexane and cyclododecane to the corresponding linear diacids, adipic acid and dodecanoic acid.

According to one preferred embodiment of the invention, it relates to the direct oxidation of cyclohexane to adipic acid, by a gas containing oxygen, in a liquid medium and in the presence of a catalyst. The catalyst preferentially comprises cobalt.

The oxidation reaction is carried out at a temperature of between 50° C. and 200° C. and preferably between 70° C. and 180° C. It may be carried out at atmospheric pressure. However, it is generally carried out under pressure in order to keep the components of the reaction medium in liquid form. The pressure may be between 10 KPa (0.1 bar) and 20 000 KPa (200 bar) and preferably between 100 KPa (1 bar) and 10 000 KPa (100 bar).

The oxygen used may be in pure form or as a mixture with an inert gas such as nitrogen or helium. Air which is more or less enriched with oxygen may also be used. The amount of oxygen fed into the medium is advantageously between 1 and 1 000 mol per mole of compounds to be oxidized.

The oxidation process may be performed continuously or according to a batchwise process. The liquid reaction medium leaving the reactor is advantageously treated according to known processes for, firstly, separating out and recovering the acid produced and, secondly, recycling the unoxidized or partially oxidized organic compounds such as cyclohexane, cyclohexanol and/or cyclohexanone, the catalyst and the lipophilic acidic compound.

The amount of catalyst, expressed as a percentage by weight of cobalt relative to the reaction mixture, is generally between 0.00001% and 5% and preferably between 0.001% and 2%, without these values being critical. However, it is a matter of having a sufficient activity while at the same time not using excessively large amounts of a catalyst which must then be separated from the final reaction mixture and recycled.

Besides cobalt, the catalyst may also comprise other compounds based on metals chosen from the group comprising manganese, copper, cerium, vanadium, chromium, zirconium and hafnium or a combination of some of these elements.

It is advantageous also to use a compound which initiates the oxidation reaction, such as, for example, a ketone or an aldehyde. Cyclohexanone, which is a reaction intermediate in the case of the oxidation of cyclohexane, is most particularly indicated. Generally, the initiator represents from 0.01% to 20% by weight relative to the weight of the reaction mixture used, without these proportions having a critical value. The initiator is especially useful during the start of the oxidation and when the oxidation is carried out at a temperature below 120° C. It may be introduced from the start of the reaction.

The oxidation may also be carried out in the presence of water introduced from the initial stage of the process.

As indicated above, the reaction mixture obtained after the oxidation is subjected to various operations to separate out some of its constituents in order, for example, to allow them to be recycled into the oxidation and to allow the acids produced to be recovered.

According to a first variant of the process, the crude reaction mixture is first subjected to cooling to a temperature of from 16° C. to 30° C., for example, which brings about crystallization of at least some of the acid formed. A medium is thus obtained comprising a solid phase consisting essentially of acid, at least one liquid organic phase essentially containing the unreacted compound to be oxidized, possibly the lipophilic acidic compound and the oxidation intermediates (or several organic phases if the lipophilic acidic compound and the hydrocarbon are not fully miscible at low temperature) and a liquid aqueous phase essentially containing acidic oxidation by-products and the water formed. The catalyst may be in one of the organic phases if it is soluble in the said phase, or in the lower aqueous phase.

After filtering off or centrifuging the solid, the organic and aqueous liquid phases consisting of the filtrate or the centrifugate are separated by settling, if need be: the organic phase(s) may be recycled into a further oxidation reaction.

It may be advantageous, prior to the operation to crystallize the acid, to carry out a concentration of the reaction mixture.

According to a second variant of the process, the final crude reaction mixture may be removed while hot, for example at a temperature which may be up to 75° C. The reaction mixture then separates by settling into at least two liquid phases: one or more organic phases essentially containing the unreacted hydrocarbon, the lipophilic acidic compound and the oxidation intermediates, and an aqueous liquid phase essentially containing the acids formed and the water formed. Depending on the solubility and nature of the catalyst, it may be present in the organic phase(s), recovered by solid/liquid separation before precipitation or crystallization of the acid formed in the case of a heterogeneous catalysis, or, if it is soluble in the aqueous phase, it may be extracted by liquid/liquid extraction, on resin or electrodialysis.

As in the first variant, the liquid phases are separated by settling: the organic phase(s) may be recycled into a further oxidation reaction.

In these embodiments, the lipophilic acidic compound used in accordance with the invention is generally contained in or forms an essential element of the organic phase(s). Consequently, after separating out the acid formed and optionally the liquid phase containing the water formed, the oxidation by-products and the catalyst, the lipophilic acidic compound is recycled into the oxidation step with the hydrocarbon which has not been oxidized and the oxidation intermediates.

Moreover, if the lipophilic acidic compound is solid in one phase of treatment of the reaction medium, it will be advantageously separated out and recovered by carrying out solid/liquid separation processes either before treating the reaction medium to recover the acid produced, or with the acid produced. In this latter case, the acid produced may be recovered by extraction with water.

In these embodiment examples of the invention, water may be added to the reaction medium in order to obtain better dissolution of the acidic oxidation by-products and better recovery of the acid formed.

The acid is generally recovered by precipitation during the cooling of the reaction medium. The acid thus recovered may be purified according to usual techniques disclosed in numerous patents. Mention may be made, for example, of French patents Nos. 2 749 299 and 2 749 300.

If the non-organic or aqueous liquid phase contains the catalyst, this catalyst is extracted either before crystallization of the acid formed by precipitation or extraction according to known processes such as liquid/liquid extraction, electrodialysis or treatment on ion-exchange resins, for example, or after crystallization of the acid formed by extraction techniques described above or the like.

Other advantages and details of the invention will emerge more clearly in the light of the examples below, which are given purely for indicative and illustrative purposes.

EXAMPLE 1

Preparation of Cobalt(II) 3.5-di-tert-butylbenzoate 2.42 g (10.3 mmol) of 3,5-di-tert-butylbenzoic acid are dissolved in 60 ml of cyclohexane at room temperature (colourless solution). In parallel, an aqueous solution consisting of 10 ml of water and 0.42 g of sodium hydroxide (10.5 mmol) is prepared and 1.28 g (5.13 mmol) of cobalt acetate tetrahydrate dissolved in 10 ml of water (pink solution) are added thereto.

The aqueous solution is added to the cyclohexane solution with stirring, at room temperature. After 3 h, the aqueous phase is colourless and the cyclohexane phase is blue.

After separating the two phases by settling and removing the cyclohexane by concentration, 2.69 g of blue crystals of cobalt 3,5-di-tert-butylbenzoate are recovered (M=525.5).

EXAMPLE 2

The following are loaded into a 125 ml titanium autoclave fitted with means of heating via a heating collar, a turbo-mixer and means of introducing gas and of pressure regulation:
- 40.68 g (484.3 mmol) of cyclohexane
- 4.87 g (33 mmol) of 2-ethylhexanoic acid
- 0.4811 g (4.91 mmol) of cyclohexanone
- 0.42 g (0.80 mmol of Co) of cobalt 3,5-di-tert-butylbenzoate of Example 1.

After closing the reactor, the mixture is stirred at 1 000 rpm, an air pressure (100 bar at 20° C.) is created and the mixture is heated. The temperature reaches 105° C. in the bulk in 10 min and this temperature is maintained for a further 3 hours.

After cooling and depressurization, the reaction mixture comprises a phase comprising cyclohexane and a precipitate.

After separating out the cyclohexane phase, the precipitate is dissolved in acetic acid. The cyclohexane phase and the acetic solution are analysed by gas chromatography, and the results are collated in Table I below.

The degree of conversion (DC) of the cyclohexane is: 2.0%.

TABLE I

| Products | Cyclohexane phase mmol | Acetic solution mmol | Total mmol | CS % |
| --- | --- | --- | --- | --- |
| Cyclohexanone* | 6.13 | 0.21 | 1.42* | 14.3 |
| Cyclohexanol | 5.45 | 0.19 | 5.64 | 57.0 |
| Butyrolactone | 0.08 |  | 0.08 | <1 |
| Valerolactone | 0.05 |  | 0.05 | <1 |
| Succinic acid | traces | traces | traces | <1 |
| Glutaric acid | 0.17 | 0.24 | 0.41 | 4.1 |
| Adipic acid | 0.38 | 1.92 | 2.30 | 23.2 |

*cyclohexanone assayed-initial cyclohexanone = cyclohexanone formed.
CS % = selectivity towards the compound indicated in the 1st column relative to the cyclohexane converted.

Comparative Test 2

Example 2 is repeated in the same apparatus and under the same operating conditions, except that no 2-ethylhexanoic acid is loaded and an amount of 40.2 g (479 mmol) of cyclohexane is used.

The following results (Table II) are obtained:

Degree of conversion (DC) of the cyclohexane: 0.55%

TABLE II

| Products | Total mmol | CS % |
| --- | --- | --- |
| Cyclohexanone | 0.83* | 31.4 |
| Cyclohexanol | 1.61 | 61.0 |
| Butyrolactone | 0.07 | 2.7 |
| Valerolactone | 0.06 | 2.2 |
| Succinic acid | traces |  |
| Glutaric acid | traces |  |
| Adipic acid | 0.07 | 2.7 |

*cyclohexanone assayed-initial cyclohexanone = cyclohexanone formed

EXAMPLES 3 TO 5

Example 2 is repeated, but with variable amounts of 2-ethylhexanoic acid.

Table III below gives the amounts of products used in each example, and Table IV collates the results obtained by analysis of the oxidation medium after reaction, according to the method described in Example 2.

TABLE III (expressed in g)

| | Example 3 | | | | Example 4 | | | | Example 5 | | |
|---|---|---|---|---|---|---|---|---|---|---|---|
| Cyclo | Co | -one | Acid | Cyclo | Co | -one | Acid | Cyclo | Co | -one | Acid |
| 40.36 | 0.1036 | 0.503 | 0 | 40.17 | 0.1070 | 0.459 | 3.70 | 22.07 | 0.1036 | 0.4963 | 19.96 |

Cyclo=cyclohexane
Co=catalyst expressed as g of catalyst of Example 1
-one=cyclohexanone
-ol=cyclohexanol
Acid=hexanoic acid The degrees of conversion of the cyclohexane are:

Example 3: 0.52%

Example 4: 1.85%

Example 5: 2.26%

TABLE IV

| | Example 3 | | Example 4 | | Example 5 | |
|---|---|---|---|---|---|---|
| Products | Total mmol | CS % | Total mmol | CS % | Total mmol | CS % |
| Cyclohexanone* | 0.6* | 23.8 | 1.56* | 17.6 | 0.16* | 2.7 |
| Cyclohexanol | 1.79 | 71.0 | 5.12 | 57.9 | 2.74 | 46.1 |
| Butyrolactone | | | 0.06 | <1 | 0.11 | 1.9 |
| Valerolactone | | | 0.06 | <1 | | |
| Succinic acid | | | | | 0.18 | 3.0 |
| Glutaric acid | | | 0.33 | 3.7 | 0.75 | 12.6 |
| Adipic acid | 0.13 | 5.2 | 1.71 | 19.3 | 2.00 | 33.7 |

*cyclohexanone assayed-initial cyclohexanone = cyclohexanone formed.

The results of the analysis of the reaction medium are given in Table V below.

TABLE V

| Products | Total mmol | CS % |
|---|---|---|
| Cyclohexanone* | 1.4 | 23.2 |
| Cyclohexanol | 3.76 | 62.4 |
| Butyrolactone | | |
| Valerolactone | | |
| Succinic acid | | |
| Glutaric acid | 0.11 | 1.8 |
| Adipic acid | 0.76 | 12.6 |

*cylohexanone assayed-initial cyclohexanone = cyclohexanone formed.

EXAMPLES 7 TO 14

The procedure of Example 2 is repeated. The tests below were carried out using 0.39 g (4 mmol) of cyclohexanone and a weight of catalyst consisting of the acetylacetonate of cobalt in oxidation state 3 to have a concentration, expressed as cobalt, of 1 500 mg/kg of reaction medium.

The amounts of cyclohexane and of lipophilic acidic compounds used are indicated in Table VI below, which also collate the results of the analysis of the reaction media obtained.

TABLE VI

| Examples | Octanoic acid/Co (mol) | Cyclohexane used mmol | Cyclohexane converted mmol | DC % cyclohexane | CS adipic acid % | CS -one % | CS -ol % |
|---|---|---|---|---|---|---|---|
| 7 | 0 | 479 | 4.0 | 0.84 | 6.0 | 37.6 | 75.5 |
| 8 | 26.3 | 470.4 | 10.6 | 2.25 | 12.7 | 29.9 | 51.9 |
| 9 | 13.7 (Co 3 000 ppm) | 430.4 | 16.3 | 3.8 | 15.7 | 33.7 | 43.8 |
| 10 | 7.0 (Co 6 000 ppm) | 428.8 | 21.9 | 4.8 | 15.3 | 38.7 | 45.0 |
| 11 | 58.3 | 396.9 | 13.1 | 3.3 | 29.6 | 12.7 | 43.8 |
| 12 | 77.9 | 334.6 | 19.4 | 5.8 | 54.5 | 0 | 27.3 |
| 13 | 114.2 | 287.3 | 17.5 | 6.1 | 71.9 | 0 | 22.2 |
| 14 | 174.9 | 193 | 12.25 | 6.35 | 72.0 | 0 | 21.4 |

CS -one: selectivity towards cyclohexanone relative to the number of moles of cyclohexane converted.
CS -ol: selectivity towards cyclohexanol relative to the number of moles of cyclohexane converted.

EXAMPLE 6

Example 2 is repeated, but using the following starting materials:

40.34 g (480.37 mmol) of cyclohexane,
0.4688 g (478 mmol) of cyclohexanone,
2.67 g (11.4 mmol) of 3,5-di-tert-butylbenzoic acid,
0.1078 g (0.205 mmol of Co) of cobalt 3,5-di-tert-butylbenzoate.

The degree of conversion (DC) of the cyclohexane is 1.26%.

EXAMPLES 15 TO 20

The procedure of Example 2 is repeated. The tests below were carried out using 0.39 g (4 mmol) of cyclohexanone and a weight of catalyst, consisting of acetylacetonate of cobalt in oxidation state 3, to have a concentration, expressed as cobalt in mg/kg of reaction medium, indicated in Table VII below.

The amounts of cyclohexane and of lipophilic acidic compounds (octanoic acid) used are also indicated in Table VII below, which also collate the results of the analysis of the reaction media obtained. The reaction temperature is 105° C. for all these tests.

In each test, an additive comprising hydroxyl and imide functions was added in an amount indicated in Table VII below. These additives are:

N-hydroxysuccinimide (NHS)
N-hydroxyphthalimide (NHPI)

TABLE VII

| Examples | Octanoic acid (mmol)/Co (ppm) | Cyclohexane used mmol | Additives (mmol) | Time (min) | Cyclohexane converted mmol | DC % cyclohexane | CS adipic acid % | CS - one % | CS - ol % |
|---|---|---|---|---|---|---|---|---|---|
| 15 | 86.9 1460 | 450 | NHPI 4.58 | 180 | 51.6 | 11.4 | 21.3 | 58.4 | 13.6 |
| 16 | 86.9 1460 | 451 | NHS 4.75 | 180 | 36.9 | 8.2 | 17.7 | 53.3 | 29.8 |
| 17 | 86.9 1430 | 448 | NHS 2.1 | 180 | 38 | 8.5 | 18.4 | 51 | 21.8 |
| 18 | 86.9 1460 | 447 | NHPI 8.75 | 40 | 46.9 | 10.5 | 23.2 | 59 | 10.6 |
| 19 | 138.6 | 361 | NHPI 8.65 | 25 | 45.1 | 12.5 | 27.3 | 55.8 | 9.9 |
| 20 | 86.8 1500 1080 ppm Ce | 446 | NHPI 8.65 | 40 | 38 | 8.5 | 29.6 | 35.7 | 22.7 |

EXAMPLE 21

Example 8 was repeated, but using as lipophilic acidic compound palmitic acid instead of octanoic acid.

Table VIII collates the amounts of cyclohexane and of acidic compounds used and the analysis of the medium obtained after oxidation.

TABLE VIII

| Example | Palmitic acid/Co (mol) | Cyclohexane used mmol | Cyclohexane converted mmol | DC % cyclohexane | CS adipic acid % | CS - one % | CS - ol % |
|---|---|---|---|---|---|---|---|
| 21 | 16.4 | 429.9 | 9.1 | 2.1 | 9.2 | 32.3 | 54.1 |

EXAMPLE 22

Test 8 is repeated, but adding ferric acetylacetonate to the cobalt compound in order to obtain 250 ppm of Fe in the medium.

The amounts of products and the results of the analysis of the reaction medium obtained are collated in Table IX.

TABLE IX

| Ex. | Co-catalyst | Octanoic acid/Co (mol) | Cyclohexane used mmol | Cyclohexane converted mmol | DC % cyclohexane | CS adipic acid % | CS - one % | CS - ol % |
|---|---|---|---|---|---|---|---|---|
| 22 | Fe(acac)3, [Fe] = 250 ppm | 17.5 | 432.5 | 14.42 | 3.35 | 18.9 | 30.1 | 40.6 |

EXAMPLE 23

Test 22 was repeated, but replacing the ferric acetylacetonate co-catalyst with chromium acetylacetonate in order to obtain 53 ppm of Cr in the medium. The reaction time was increased to 6 hours.

The amounts of products and the results of the analysis of the reaction medium obtained are collated in Table X below.

TABLE X

| Example | Co-catalyst | Octanoic acid/Co (mol) | Cyclohexane used mmol | Cyclohexane converted mmol | DC % | CS adipic acid % | CS - one % | CS - ol % |
|---|---|---|---|---|---|---|---|---|
| Comparative | O | 28.4 | 430 | 17.4 | 4.05 | 12.1 | 38.5 | 43.9 |
| 23 | Cr(OAc)3 [Cr] = 53 ppm | 28.4 | 430 | 19.3 | 4.5 | 16 | 37.6 | 38.8 |

EXAMPLES 24 TO 26

Example 8 was repeated, but using as lipophilic acidic compounds p-chlorobenzoic acid or a mixture of this acid with octanoic acid.

The amounts of products and the results of the analysis of the reaction media obtained are collated in Table XI below.

TABLE XI

| Example | p-chlorobenzoic acid/Co (mol) | Octanoic acid/Co (mol) | Cyclohexane used mmol | Cyclohexane converted mmol | DC % | CS adipic acid % | CS -one % | CS -ol % |
|---|---|---|---|---|---|---|---|---|
| 24 | 6.5 | 27.9 | 241.5 | 12.4 | 2.9 | 14.7 | 28.5 | 48.4 |
| 25 | 6.6 | 0 | 476.9 | 11.0 | 2.3 | 7.6 | 33.3 | 53.8 |
| 26 | 2.4 | 0 | 432.6 | 11 | 2.6 | 6.1 | 34.9 | 54.4 |

The invention claimed is:

1. Process comprising oxidizing cycloaliphatic hydrocarbons to dicarboxylic acids in a liquid medium by an oxidizing agent selected from the group consisting of oxygen, air and mixtures of oxygen with nitrogen or an inert gas, wherein one of the constituents of the liquid medium is a lipophilic acidic organic compound selected from the group consisting of 2,5-di-tert-butylbenzoic acid, 4-tert-butylbenzoic acid, 4-octylbenzoic acid, tert-butyl hydrogen orthophthalate and naphthenic and anthracenic acids substituted with tert-butyl groups, wherein the hydrocarbon to be oxidized is at least partially miscible with the lipophilic acidic compound, under the conditions in which the oxidation reaction is carried out, and wherein the weight percentage of lipophilic acidic compound is between 10% and 80% by weight relative to the total weight of the liquid medium, the oxidation being conducted at a temperature within the range of 50° C. to 200° C. and a pressure within the range of 0.1 bar and 200 bar.

2. Process according to claim 1, wherein the oxidation is carried out in the presence of a catalyst.

3. Process according to claim 2, wherein the catalyst is soluble in the liquid medium under the conditions in which the oxidation reaction is carried out.

4. Process according to claim 2, wherein the catalyst is insoluble in the liquid medium under the conditions in which the oxidation reaction is carried out.

5. Process according to claim 4, wherein the catalyst is a supported catalyst comprising a mineral or polymeric support.

6. Process according to claim 1, wherein the oxidation is carried out in the presence of a compound selected from the family consisting of nitriles, hydroxyimide compounds and halogenated compounds.

7. Process according to claim 6, wherein said compound is a nitrile compound selected from the group consisting of acetonitrile and benzonitrile.

8. Process according to claim 6, wherein said compound is a hydroxyimide compound selected from the group consisting of N-hydroxysuccinimide and N-hydroxyphthalimide.

9. Process according to claim 6, wherein said compound is a halogenated compound selected from the group consisting of cyclic fluoroaliphatic hydrocarbons, acyclic fluoroaliphatic hydrocarbons, perfluoroaliphatic hydrocarbons, fluoroaromatic hydrocarbons, fluoro esters, perfluoro esters, fluoro ketones, perfluoro ketones, fluoronitriles, perfluoronitriles, fluoro acids, perfluoro acids, fluoro halides, perfluoro halides, perfluorobromooctane, fluoroamines, and perfluoroamines.

10. Process according to claim 1, wherein the hydrocarbon to be oxidized is selected from the group consisting of cyclohexane and cyclododecane.

11. Process according to claim 10, wherein the acid produced is adipic acid or dodecanedioic acid.

12. Process according to claim 1, wherein, after oxidation, the phases of the liquid medium are separated by settling into at least one organic phase formed by the unoxidized hydrocarbon, the lipophilic acidic compound, said organic phases being recycled into a further oxidation and the acid produced being extracted from the aqueous phase.

13. Process according to claim 12, wherein the acid is extracted from the aqueous phase by crystallization.

14. Process according to claim 4, wherein the catalyst is recycled with the organic phase(s).

15. Process according to claim 5, wherein the catalyst is separated from the liquid medium by separation of the phases by settling or by solid/liquid separation.

16. Process according to claim 12, wherein the catalyst which is soluble in the aqueous phase is extracted by liquid/liquid extraction, separation on resins by electrodialysis.

17. Process according to claim 1, wherein a catalyst comprises cobalt as catalytically active element.

* * * * *